United States Patent [19]

Tennant

[11] Patent Number: 4,755,171

[45] Date of Patent: Jul. 5, 1988

[54] TUBULAR SURGICAL DEVICE

[76] Inventor: Jerald L. Tennant, 806 Greentree La., Duncanville, Tex. 75137

[21] Appl. No.: 56,404

[22] Filed: May 29, 1987

[51] Int. Cl.$^4$ .............................................. A61M 31/00
[52] U.S. Cl. ..................................... 604/93; 604/280; 604/275
[58] Field of Search .................... 604/93, 48, 54, 280, 604/275, 282, 285, 265, 264; 128/207.14

[56] References Cited

U.S. PATENT DOCUMENTS

| | | |
|---|---|---|
| 1,596,754 | 8/1926 | Moschelle . |
| 3,399,668 | 9/1968 | Lundgren ............................. 128/2 |
| 3,566,874 | 3/1971 | Shepherd . |
| 3,861,396 | 1/1975 | Vaillancourt et al. . |
| 4,026,296 | 5/1977 | Stoy et al. . |
| 4,055,682 | 10/1977 | Merrill ................................. 427/2 |
| 4,498,473 | 2/1985 | Gereg ............................ 604/282 X |

FOREIGN PATENT DOCUMENTS 2554352  5/1985  France ................. 604/280

Primary Examiner—Stephen C. Pellegrino
Attorney, Agent, or Firm—Richards, Harris, Medlock & Andrews

[57] ABSTRACT

A tubular surgical device (10) is provided for insertion into a cavity of a living body. The device (10) includes an elongated substantially hollow cylindrical tubular flexible conduit (12) having an exterior surface (14) for contact with the tissue of the cavity. The external surface (14) is coated with a hydrophilic material and is impregnated with an infection preventing material for absorption by the tissue of the cavity. The conduit (12) includes a bore (20) which is defined by an annular wall (22). The annular wall includes a plurality of axially spaced alternating annular ridges (24) and grooves (26) to render the conduit (12) flexible. A delivery system (42, 44, 46) is provided for the tubular surgical device (10) for supplying, replenishing, and delivering antibiotics and germicides to conduit (12) for absorption by the cavity tissue.

8 Claims, 1 Drawing Sheet

TUBULAR SURGICAL DEVICE

TECHNICAL FIELD

This invention relates to tubular surgical devices designed to be temporarily introduced into cavities of a living body, such as a catheter, tracheal or gastric intubation or sounding tube, cystoscope and the like, and more particularly to a tubular surgical device which is provided with a replenishable supply of antibiotics and germicides.

BACKGROUND ART

During the course of numerous medical and surgical techniques, it is common to drain fluids from various cavities as well as to inject fluids into cavities. It is common to place a tube through the nose and esophagus into the stomach to keep the stomach pumped dry during surgery on the abdomen or intestines. Tubes are inserted into the urinary bladder to drain urine when a patient does not have normal bladder function, and tubes are placed into the abdomen and/or chest to drain fluid in various disease states.

Various types of tubes or catheters have been proposed and have been manufactured from various types of plastic material. Problems have developed with such tubes in that the tube material irritated the surrounding cavity tissue and that the tubes would collapse upon the application of suction. Additionally, existing tubes are generally rigid making it difficult to insert a catheter where curves are present such as, for example, where a catheter is placed upward through the nose, around the pharynx and down through the esophagus.

A need has thus arisen for a tubular surgical device that can be easily inserted into a cavity of the body, does not collapse under suction and which does not cause irritation and infection of the surrounding cavity tissue.

DISCLOSURE OF THE INVENTION

In accordance with the present invention, a tubular surgical device is provided for substantially eliminating the problems heretofore associated with tubular devices such as catheters.

In accordance with the present invention, a tubular surgical device for insertion into cavities of a living body is provided. The tubular device includes an elongated substantially hollow cylindrical tubular flexible conduit having an external surface for contact with tissue of the cavity. The conduit includes an axially extending bore, extending the length of the conduit and being defined by an annular wall interior of the conduit. The annular wall includes a plurality of axially spaced alternating annular ridges and grooves to render the conduit flexible in the area of the ridges and grooves for insertion into the cavity.

In accordance with another aspect of the present invention, a tubular surgical device for insertion into cavities of a living body is provided. The tubular device includes an elongated substantially hollow cylindrical tubular flexible conduit having an exterior surface for contact with tissue of the cavity. The external surface of the conduit is coated with a hydrophilic material which is impregnated with an infection preventing material for absorption by the tissue of the cavity. The conduit includes an axially extending bore which extends the length of the conduit and which defines an annular wall interior of the conduit. The annular wall includes a plurality of axially spaced alternating annular ridges and grooves to render the conduit flexible in the area of said ridges and grooves for easy insertion of the conduit into the cavity. The tubular device further includes a channel surrounding the bore and disposed adjacent to the annular wall for delivering and replenishing the infection preventing material to the exterior surface of the conduit.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION

Figure 1:
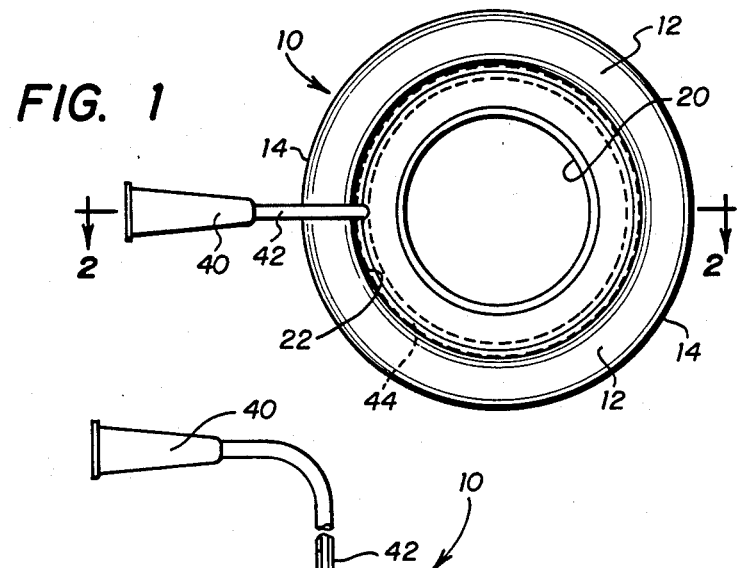
FIG. 1 is a top plan view of the present tubular surgical device.
Figure 3:
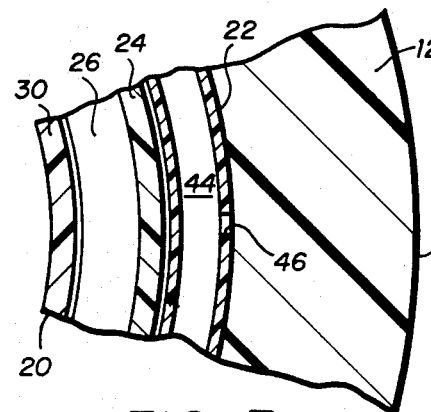
FIG. 3 is a cross-sectional view taken generally along sectional lines 3—3 of the tubular surgical device illustrated in FIG. 2.
Figure 2:
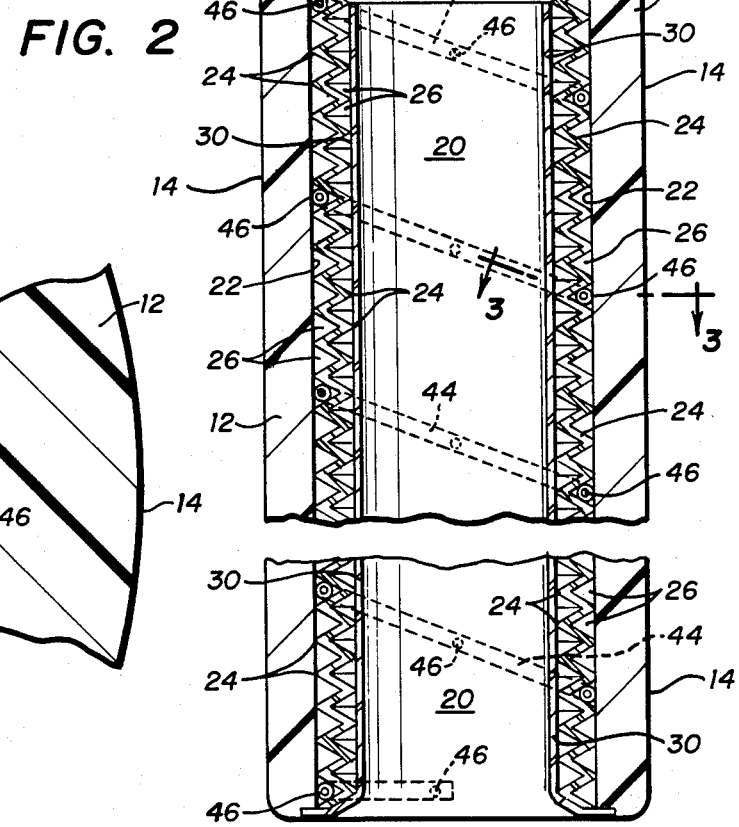
FIG. 2 is a cross-sectional view taken generally along sectional lines 2—2 of the tubular surgical device illustrated in FIG. 1.

Referring simultaneously to FIGS. 1, 2 and 3, the present tubular surgical device is illustrated and is generally identified by the numeral 10. Tubular surgical device 10 is designed to be temporarily introduced into cavities of a living body and include such uses as, for example, a catheter, tracheal or gastric intubation sounding tube, cystoscope and the like. Typically, the cavity tissue surrounds the surgical device.

Tubular surgical device 10 includes an elongated hollow cylindrical tubular conduit generally identified by the numeral 12. Conduit 12 includes an exterior surface 14. In accordance with the present invention, exterior surface 14 is provided with a coating of hydrophilic material such as, for example, a hydrophilic acrylate material. The use of the hydrophilic material coating on exterior surface 14 of conduit 12 prevents irritation to the surrounding cavity tissue. Various types of hydrophilic material are described in U.S. Pat. Nos. 3,861,396 and 3,566,874 which descriptions are incorporated herein by reference and made a part of this description.

Conduit 12 includes a centrally disposed and axially positioned bore 20 which extends the length of conduit 12. Bore 20 is defined by an annular wall 22 interior of conduit 12 and substantially parallel to exterior surface 14.

In accordance with the present invention, in order to increase the flexibility of device 10, annular wall 22 is provided with a plurality of axially spaced alternating annular ridges 24 and grooves 26. Ridges 24 and grooves 26 provide an accordion-like structure on the interior of conduit 12 and allows conduit 12 to be easily bent for insertion through various curves and body cavities.

Disposed adjacent to ridges 24 on the interior of conduit 12 is a lining member 30. Lining member 30 provides a smooth surface within conduit 12 and prevents body fluids and material from becoming lodged within grooves 26. Lining member 30 may also be coated with a hydrophobic material.

Exterior surface 14 of conduit 12 may be emersed in a solution of an antibiotic or germicide to increase the effectiveness of conduit 12 against infection. The antibiotic or germicide is retained by the hydrophilic coating even if the solution in which conduit 12 is immersed is removed. Various types of antibiotics and germicides are described in U.S. Pat. No. 3,566,874 which description is incorporated herein by reference.

An important aspect of the present invention is the use of an antibiotic and germicide delivery system to replenish the supply of infection preventing material through conduit 12 which is available to the tissue of the cavity. As illustrated in FIGS. 1 and 2, a syringe 40 can be selectively interconnected to conduit 12 via a tube 42. Tube 42 is integral to conduit 12 and is interconnected to a spiral channel 44 which is circumferentially disposed around bore 20 adjacent annular wall 22. Channel 44 extends along the length of bore 20 and includes a plurality of periodically spaced apertures 46 which lie adjacent annular wall 22. Infection preventing material such as antibiotics and germicides are introduced into channel 44 via tube 42 from syringe 40 and passes through apertures 46 to conduit 12. Conduit 12 absorbs the infection preventing material which is then passed to the tissues surrounding the cavity in which tubular surgical device 10 is inserted. The infection preventing material is uniformly distributed throughout the length of conduit 12 and can be periodically resupplied for introduction to the tissue via tube 42.

Therefore it can be seen that the present tubular surgical device prevents irritation to tissue by being coated with a hydrophilic material and is provided with a replenishable supply of antibiotic and germicide to increase the effectiveness of the present tubular device against infection. The present tubular surgical device further includes structure for rendering the tubular device flexible for easy insertion into a cavity of the body.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. A tubular surgical device for insertion into a cavity of a living body comprising:
    an elongated substantially hollow cylindrical tubular flexible conduit having an exterior surface for contact with tissue of the cavity and having an axially extending bore, said bore extending the length of said conduit and being defined by an annular wall interior of said conduit; and
    means for delivering infection preventing material to said exterior surface of said conduit while the tubular surgical device is positioned in the cavity including a channel surrounding said bore and being disposed adjacent said annular wall; said channel including a plurality of apertures in fluid communication with said conduit.

2. The tubular surgical device of claim 1 wherein said exterior surface of said tubular flexible conduit includes a coating of hydrophilic material.

3. The tubular surgical device of claim 1 wherein said exterior surface of said tubular flexible conduit includes antibiotics and germicides for preventing infection of the tissue in the cavity.

4. A tubular surgical device for insertion into a cavity of living body comprising:
    an elongated substantially hollow cylindrical tubular flexible conduit having an exterior surface for contacting tissue of the cavity;
    said exterior surface of said conduit being coated with a hydrophilic material and being impregnated with infection preventing material for absorption by the tissue of the cavity;
    said conduit having an axially extending bore, said bore extending the length of said conduit and being defined by an annular wall interior of said conduit;
    said annular wall including a plurality of axial spaced alternating annular ridges and grooves to render said conduit flexible in the area of said ridges and grooves for easy insertion of the conduit into the cavity and;
    means for delivering infection preventing material to said exterior surface of said conduit while the tubular surgical device is positioned in the cavity including a channel surrounding said bore and being disposed adjacent said annular wall; said channel including a plurality of apertures in fluid communication with said conduit.

5. The tubular surgical device of claim 4 wherein said infection preventing material is selected from the group consisting of antibiotics and germicides.

6. The tubular surgical device of claim 4 and further including:
    means disposed adjacent said annular ridges for preventing material transported by the tubular surgical device from collecting in said grooves.

7. A tubular surgical device for insertion into a cavity of a living body comprising:
    an elongated substantially hollow cylindrical tubular flexible conduit having an exterior surface for contact with tissue of the cavity;
    said exterior surface of said conduit being coated with a hydrophilic material and further being impregnated with infection preventing material selected from the group consisting of antibiotics and germicides for absorption by the tissue of the cavity;
    said conduit having an axially extending bore, said bore extending the length of said conduit and being defined by an annular wall interior of said conduit;
    said annular wall including a plurality of axially spaced alternating annular ridges and grooves to render said conduit flexible in the area of said ridges and grooves for easy insertion of the conduit into the cavity; and
    a channel surrounding said bore and being disposed adjacent said annular wall, said channel including a plurality of apertures within said conduit and said channel extending exterior of said conduit for receiving antibiotics and germicides for transporting antibiotics and germicides throughout said conduit and via said plurality of apertures to tissue in the cavity contacting said conduit exterior surface.

8. The tubular surgical device of claim 7 and further including:
    means disposed adjacent said annular ridges for preventing material transported by the surgical tubular device from collecting in said grooves.

* * * * *